(12) United States Patent
Edoga et al.

(10) Patent No.: US 7,261,705 B2
(45) Date of Patent: Aug. 28, 2007

(54) IMPLANTABLE DIALYSIS ACCESS PORT

(75) Inventors: John K. Edoga, Morristown, NJ (US); Thierry Richard, Florham Park, NJ (US)

(73) Assignee: Circuport, Inc., Morristown, NJ (US)

( * ) Notice: Subject to any disclaimer, the term of this patent is extended or adjusted under 35 U.S.C. 154(b) by 237 days.

(21) Appl. No.: 10/682,222

(22) Filed: Oct. 9, 2003

(65) Prior Publication Data

US 2004/0133173 A1    Jul. 8, 2004

Related U.S. Application Data

(60) Provisional application No. 60/417,204, filed on Oct. 9, 2002.

(51) Int. Cl.
*A61M 31/00* (2006.01)
*A61M 37/00* (2006.01)

(52) U.S. Cl. .................. 604/288.02; 604/6.16
(58) Field of Classification Search ........... 604/6.16, 604/7–9, 288.01–288.04; 623/1.24, 1.42
See application file for complete search history.

(56) References Cited

U.S. PATENT DOCUMENTS

| 4,113,806 A | 9/1978 | Watson |
| 4,221,882 A | 9/1980 | Huff ............... 525/240 |
| 4,251,646 A | 2/1981 | Smith ............. 525/88 |
| 4,296,022 A | 10/1981 | Hudson |
| 4,311,628 A | 1/1982 | Abdou-Sabet |
| 4,316,970 A | 2/1982 | Hughes ........... 525/240 |
| 4,496,350 A * | 1/1985 | Cosentino ........ 604/175 |
| 4,632,881 A | 12/1986 | Trotz et al. ........ 428/541 |
| 4,634,739 A | 1/1987 | Vassilatos ......... 525/240 |
| 4,774,277 A | 9/1988 | Janac et al. ....... 524/474 |
| 4,804,714 A | 2/1989 | Olivo ............. 525/240 |
| 4,846,806 A | 7/1989 | Wigness et al. |
| 4,892,518 A | 1/1990 | Cupp et al. |
| 4,929,681 A | 5/1990 | Bahl et al. ........ 525/240 |
| 4,950,259 A | 8/1990 | Geary et al. |
| 5,037,385 A | 8/1991 | O'Byrne |
| 5,562,617 A | 10/1996 | Finch, Jr. et al. |
| 5,562,618 A | 10/1996 | Cai et al. |
| 5,792,104 A | 8/1998 | Speckman et al. |
| 5,833,654 A | 11/1998 | Powers et al. |
| 5,944,688 A | 8/1999 | Lois |
| 6,022,335 A | 2/2000 | Ramadan |
| 6,053,891 A * | 4/2000 | DeCampli ......... 604/288.01 |
| 6,261,257 B1 * | 7/2001 | Uflacker et al. ...... 604/9 |

* cited by examiner

*Primary Examiner*—Catherine S. Williams
(74) *Attorney, Agent, or Firm*—Lerner, David, Littenberg, Krumholz & Mentlik, LLP

(57) ABSTRACT

An implantable access port in accordance with one embodiment of the invention comprises a hollow port casing having a first channel, a second channel and a third channel. A self-sealing insert may be disposed within the third channel. The implantable access port may further comprise a graft having a first branch, a second branch, and a third branch, the first branch extending from the first channel and adapted to be anastomosed to a vessel at a first location, the second branch extending from the second channel and adapted to be anastomosed to a vessel in a second location, the third branch extending at least partially into the third channel, wherein the third branch is disposed between the self-sealing insert and the hollow port casing. Methods for performing medical procedures associated with the implantable access port are also disclosed.

17 Claims, 8 Drawing Sheets

IMPLANTABLE DIALYSIS ACCESS PORT

CROSS-REFERENCE TO RELATED APPLICATIONS

This application claims the benefit of Provisional Application No. 60/417,204, entitled IMPLANTABLE DIALYSIS ACCESS PORT, filed Oct. 9, 2002, the disclosure of which is hereby incorporated herein by reference.

BACKGROUND OF THE INVENTION

The present invention relates to access ports implantable into a mammal to gain access to veins and arteries thereof. Typically, such ports are implanted for use during hemodialysis. The access ports of the present invention may be utilized as an alternative to a typical arteriovenous (hereinafter "AV") fistula, AV graft, or large central venous catheter used during modern kidney dialysis procedures. These ports are designed to raise the comfort level of a dialysis patient and to reduce the risk of access damage while also reducing the effort of the medical staff required to conduct the dialysis.

Unfortunately, a significant number of individuals suffer from decreased kidney function. If the kidney function is depreciated enough, usually to approximately 10% of normal levels, an individual must either undergo kidney dialysis procedures or receive a kidney transplant. Dialysis procedures remove toxic substances, waste, and bodily fluids from the bloodstream when the kidneys are unable to do so. Presently, two types of dialysis are commonly utilized, peritoneal dialysis and hemodialysis.

Peritoneal dialysis generally involves injecting special solutions into the abdomen of a patient through a port, or plastic tube. The special solution enters the abdomen and occupies the space around the abdominal organs known as the peritoneal cavity. Wastes, toxins, and excess bodily fluids mix with the special solution and are retained therein through osmosis. Once the special solution absorbs a sufficient amount of the wastes, toxins, and excess fluids, the combination may be drained out through the port. This process can either occur every four to six hours in a manual procedure, or continuously if used in conjunction with a cycler machine. While this procedure may usually be performed at home by the patient it will be appreciated that such a process creates a great burden on the patient, and typically interferes with normal life functioning.

Hemodialysis is conducted by circulating blood through an external filtering machine. Typically, a patient will require hemodialysis three-times per week, with each session lasting approximately four hours.

In hemodialysis, an "arterial" catheter removes blood from the body. The blood is then pumped across a semi-permeable membrane containing solutions to remove toxins, wastes, and excess bodily fluids. The cleansed blood is then returned to the body through a "venous" catheter. Other than in emergency situations, dialysis access is generally obtained through an AV fistula or AV graft. The same graft serves to both supply blood to the hemodialysis machine as well as return blood to the body. In this regard, two catheters are typically placed into the AV fistula or AV graft. The catheter closest to the heart typically serves as the "arterial" catheter, flowing blood from the body, and the downstream catheter typically serves as the "venous" catheter, returning blood to the body. Because the pressure gradient between the two needles is typically not great, the hemodialysis machine must include a pump to circulate the blood.

Because, peripheral veins are typically too small in diameter to permit the required flow of 250 milliliters of blood per minute back into the body, AV fistulas are surgically created approximately six weeks before hemodialysis begins in order to artificially enlarge a vein. This is done by joining a vein to an artery in a localized area while the patient is under anesthesia. The increased blood from the artery causes the vein to enlarge and thicken, thus permitting larger flows through the vein then would otherwise be possible. After the six weeks that the fistula needs to heal, two dialysis needles may be placed within the enlarged and thickened vein. One needle permits blood to be removed for dialysis and the other permits cleansed blood to return to the enlarged and thickened vein.

For individuals whose veins are not suitable for an AV fistula, an AV graft may be used. This procedure involves surgically grafting a portion of the patient's saphenous vein, a donor animal artery, or a synthetic conduit and using it to connect an artery to an existing vein. The grafted vein or prosthetic conduit may be double punctured to draw blood into the dialysis machine and return cleansed blood into the body.

Neither AV fistulas nor AV grafts are ideal. The resulting increased blood through the veins may cause a neo-intimal hyperplasia which could occlude the veins and lead to access loss. Additionally, the direct flow of blood from an artery into the veins puts undue strain on the local vascular system in general, and the heart in particular. Finally, because blood is both withdrawn from and returned to the body in the same AV fistula, dialysis is typically inefficient because of the phenomenon of recirculation.

Recent dialysis advances involve the implanting of dialysis access ports beneath the skin. These ports generally contain a chamber plugged with a self-sealing material, such as rubberized silicone, with a synthetic catheter extending out from within the chamber. The port is placed under the skin and the catheter is surgically implanted into a vein. A second port is similarly implanted beneath the skin and its catheter is surgically implanted into another portion of the vein. One port may then be used to remove blood for dialysis while the other port is used to return the cleansed blood back to the body.

Ports constructed in this manner tend to clot when not in use—especially from the port from which blood is being drawn. Also, because both catheters are inserted into the same vein, portions of the cleansed blood that has been returned to the body may be recycled back into the dialysis machine, making the procedure inefficient. As such, improvements have been contemplated.

One such improvement involves the implantation of a single port containing three recesses, each enclosed by self-sealing material. Two of the recesses are generally larger than the third. The larger two recesses include catheters extending from their reservoir to a vein within the body, typically the superior vena cava. The two larger recesses act in a substantially similar manner as the two separate ports previously described to remove blood for dialysis and replenish it to the body. The third recess includes two channels extending into the two larger recesses. An anti-clotting agent, such as heparin, may be deposited into the third recess where it is drawn off into the other two recesses. This helps to prevent the larger two recesses and associated catheters from clotting.

Although these devices represent improvements over the previous dialysis techniques, there remains a need for further improvement.

SUMMARY OF THE INVENTION

In accordance with one embodiment of the invention, there is disclosed an implantable access port comprising a hollow port casing having a first channel, a second channel and a third channel. A self-sealing insert may be disposed within the third channel. The implantable access port may further comprise a graft having a first branch, a second branch, and a third branch, the first branch extending from the first channel and adapted to be anastomosed to a first vessel at a first location, the second branch extending from the second channel and adapted to be anastomosed to a second vessel in a second location, the third branch extending at least partially into the third channel, wherein the third branch is disposed between the self-sealing insert and the hollow port casing.

In another embodiment, an implantable access port may comprise a hollow arterial port casing having a first arterial channel, a second arterial channel and a third arterial channel. A self-sealing arterial insert may be disposed within the third arterial channel. The implantable access port may further comprise an arterial graft having a first arterial branch, a second arterial branch, and a third arterial branch, the first arterial branch extending from the first arterial channel and adapted to be anastomosed to an artery at a first arterial location, the second arterial branch extending from the second arterial channel and adapted to be anastomosed to an artery in a second arterial location, the third arterial branch extending at least partially into the third arterial channel, wherein the third arterial branch is disposed between the self-sealing arterial insert and the arterial hollow port casing. The implantable access port may further comprise a hollow venous port casing having a first venous channel and a second venous channel. A self-sealing venous insert may be disposed within the second venous channel. The implantable access port may further comprise a venous graft having a first venous graft end in fluid communication with the first venous channel and a second venous graft end adapted to be anastomosed to a vein. The arterial hollow port casing and the venous hollow port casing may be connected to each other.

In accordance with one method of performing a medical procedure of the present invention, a first catheter may be inserted into a hollow arterial port casing implanted subcutaneously in a mammal such that blood flows continuously through portions of the hollow port casing and the first catheter is in fluid communication with the blood. The method may further comprise filtering the blood withdrawn from the first catheter and recycling the blood to a second catheter.

In another embodiment of the present invention, an implantable access port may comprise a port casing having a graft with first and second ends extending therethrough and a channel extending from within the graft to an exterior surface of the port casing. A self-sealing insert may be disposed within the channel to seal against the flow of fluid. The first end of the graft may be adapted to be anastomosed to a vessel in a first location and the second end of the graft may be adapted to be anastomosed to the vessel in a second location.

In yet another embodiment of the present invention, an implantable access port may comprise a port casing having a first channel extending therethrough and a second channel extending from the first channel to an exterior surface of the port casing. The implantable access port may further comprise a graft having a first end and a second end, the graft disposed within the first channel of the port casing such that the first end and the second end are exterior to the port casing. A self-sealing insert adapted to prevent fluid from passing may be disposed within the second channel. The first end and the second end of the graft may be adapted to be anastomosed to an artery such that blood will continuously flow through the port casing.

In still another embodiment of the present invention, an implantable access port may comprise first and second port halves capable of being connected to each other and a port core adapted to be disposed between the first and second port halves when the first and second port halves are connected to each other. The first and second port halves each may comprise a first recess channel and a second recess channel, wherein the first recess channel of the first port half and the first recess channel of the second port half generally form a shaped opening when the first and second port halves are connected to each other and the second recess channel of the first port half and the second recess channel of the second port half generally form a chamber in which the port core is disposed when the first and second port halves are connected to each other. The port core may further comprise an upper section having an aperture filled with a self-sealing insert and a lower section having an aperture with a graft disposed therethrough, the graft may extend from within the shaped opening when the first and second port halves are connected to each other.

In another method of implanting an implantable access port of the present invention, the method may comprise severing an artery such that the artery comprises a first end and a second end. Anastomosing a graft to the first end and the second end of the artery such that blood may flow continuously through the graft, wherein the graft is a component of a port core comprising an upper portion having an aperture extending into the graft, the aperture being partially filled with a self-sealing insert. The method may further comprise connecting a first port half and a second port half around the port core to form the complete implantable port.

BRIEF DESCRIPTION OF THE DRAWINGS

The subject matter regarded as the invention is particularly pointed out and distinctly claimed in the concluding portion of the specification. The invention, however, both as to organization and method of operation, together with features, objects, and advantages thereof may best be understood by reference to the following detailed description when read with the accompanying drawings in which:

DETAILED DESCRIPTION

Figure 1:
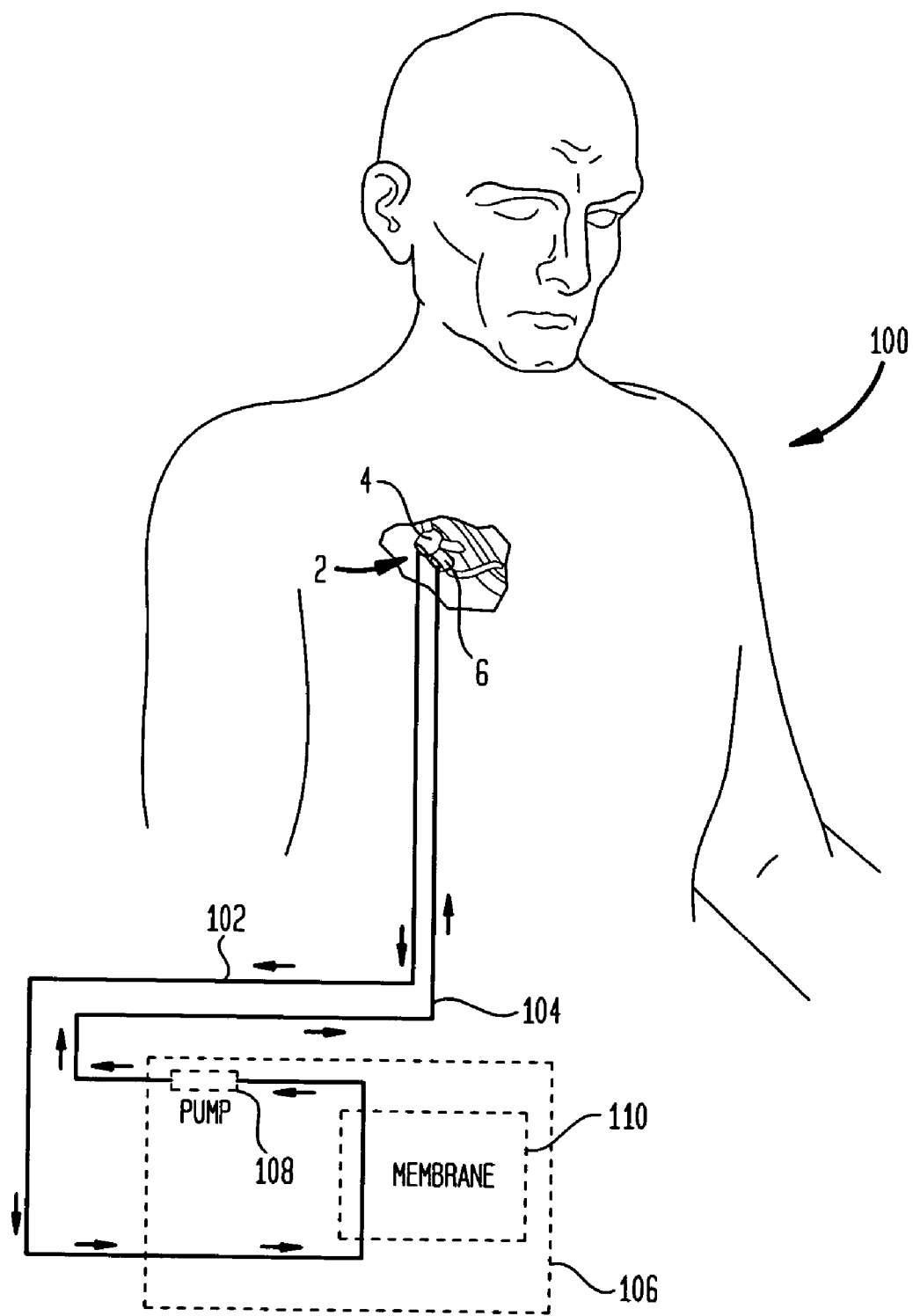
FIG. 1 is a diagrammatic view of a hemodialysis system utilizing one embodiment of the implantable access port of the present invention.

In the following is described the embodiments of the implantable dialysis access port of the present invention. In describing the embodiments illustrated in the drawings, specific terminology will be used for the sake of clarity. However, the invention is not intended to be limited to the specific terms so selected, and it is to be understood that each specific term includes all technical equivalents that operate in a similar manner to accomplish a similar purpose.

Referring to the figures, FIG. 1 depicts a diagrammatic view of a typical hemodialysis system utilizing one embodiment of the implantable dialysis access port 2 of the present invention. As shown in FIG. 1, the implantable dialysis port 2 may be implanted into the chest area 100 of the human body. The implantable dialysis port 2 may also be implanted into other areas of the body, so long as it is implanted in reasonable proximity to a medium sized artery, typically between 6 and 8 mm, for use with the implantable dialysis port 2. As will be discussed, the implantable dialysis port preferably comprises an arterial port 4 and a venous port 6 connected to each other in a single structure. In other embodiments, the ports 4, 6 may be separate structures which may include features to permit their attachment to each other.

Figure 1A:
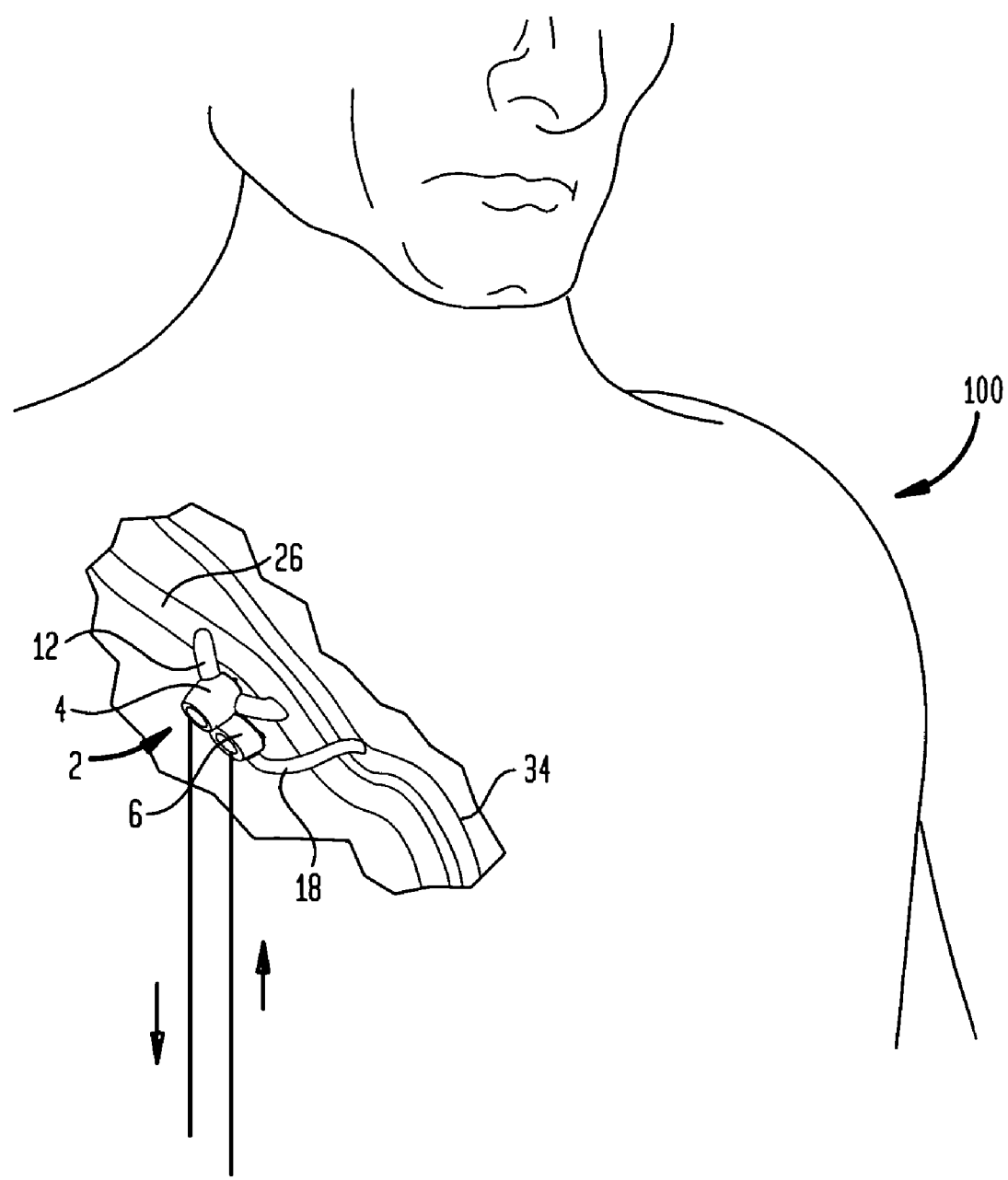
FIG. 1a is a partial blow-up view of the hemodialysis system utilizing one embodiment of the implantable access port of the present invention shown in FIG. 1.

As shown more particularly in FIG. 1a, an arterial graft 12 generally extends through the arterial port 4 while a venous graft 18 extends from the venous port 6. During the implantation process, the arterial graft 12 is preferably connected at each of its ends to the sidewall of an artery 26 while the end of the venous graft 18 is connected to a vein 34. In other embodiments, the arterial graft 12 may be connected to the artery 26 by a pair of end-to-end anasomoses. Additionally, the venous graft 18 may take the form of a venous catheter which is inserted into the vein 34 such that it may enter the central venous system.

As will be discussed in greater detail below, dialysis may be conducted by tapping the arterial port 4 with an arterial catheter 102 and the venous port with a venous catheter 104. Each of the arterial and venous catheters 102, 104 are connected to a dialysis machine 106 comprising a pump 108 and a membrane 110. Blood is permitted to flow from the artery 26 into the arterial port 4 and through the arterial catheter 102 into the membrane 110 of the dialysis machine 106 for cleansing. The pump 108 then drives the blood through the venous catheter 104 and the venous port 6 into the vein 34. Other than the use of the implantable dialysis port of the present invention, this dialysis technique is similar to that presently utilized in the art. In addition, it will be appreciated that dialysis machines 106 may have pumps 108 in series prior to the membrane 110, rather than after as previously discussed. Because of the pressure gradient between the arterial and venous systems inherent in a mammal, it may also be possible that no pump 108 is required as the patient's heart may be sufficient to circulate blood through the dialysis machine 106 as well as the patient's body.

Figure 2:
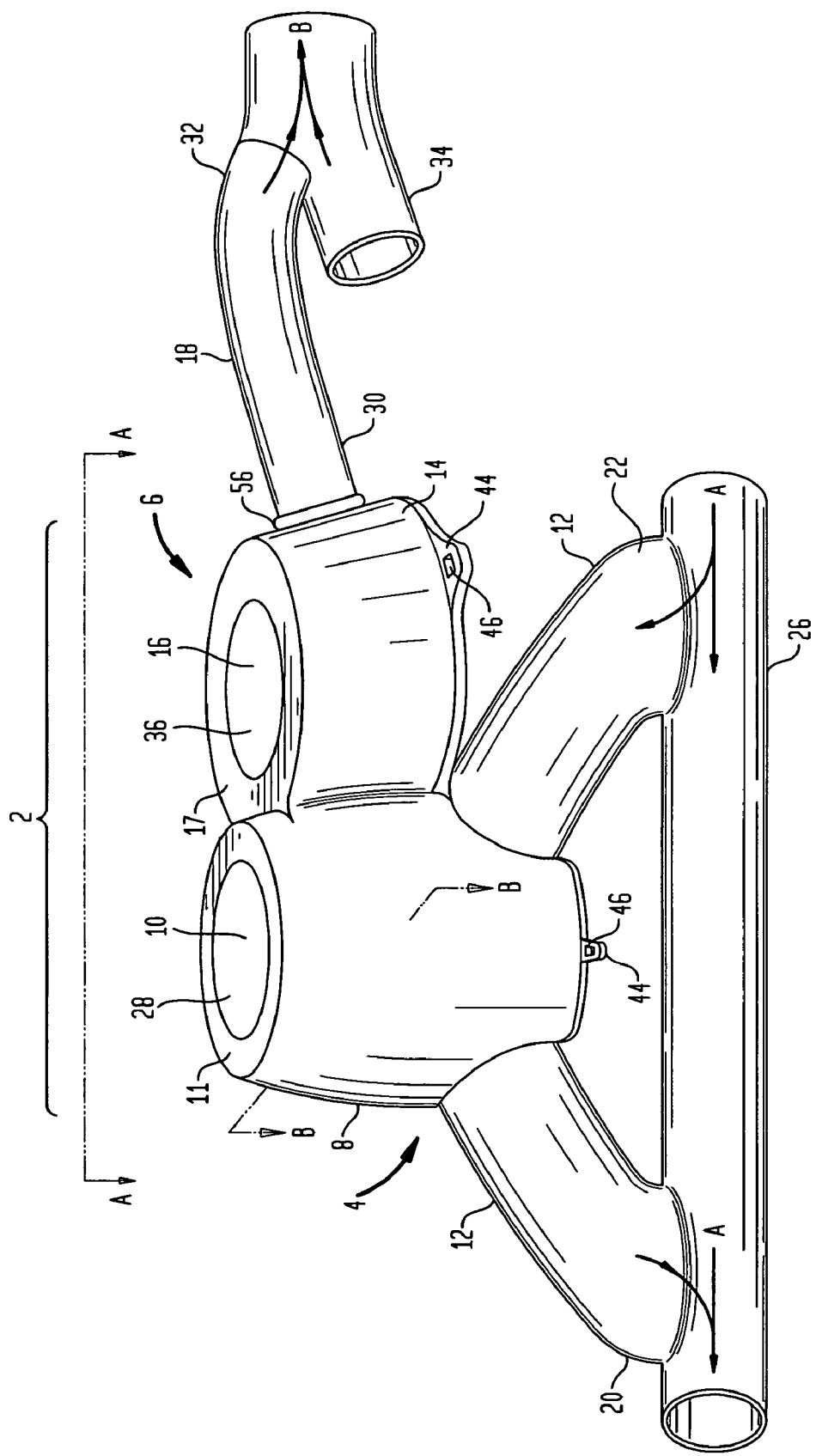
FIG. 2 is a perspective view of an implantable access port in accordance with one embodiment of the present invention shown attached to an artery and a vein.

FIG. 2 depicts a perspective view of an implantable dialysis access port 2 as it is intended to be installed in the human body in accordance with the first embodiment of the present invention. As previously discussed, the implantable dialysis access port 2 preferably comprises an arterial port 4 and a venous port 6 connected to each other or formed together. The arterial port 4 includes an arterial port casing 8 having an opening 10 through its upper surface 11. An arterial graft 12 extends through the arterial port casing 8. The venous port 6 includes a venous port casing 14 having an opening 16 through its upper surface 17. A venous graft 18 extends from the venous port casing 14.

The arterial graft 12 comprises a first end 20, a second end 22 and midsection (not shown). The first end 20 and second end 22 are each exterior to the arterial port 4 while the midsection (not shown) is disposed within the arterial port casing 8 and in direct fluid communication with opening 10. The first end 20 of the arterial graft 12 may be grafted to a medium-sized artery 26 within the human body. This graft is conducted in a surgical procedure and is typically an end to side anastomosis. Procedures of this type are well known in the art. Similarly, second end 22 of arterial graft 12 may be grafted to a second portion of artery 26. This graft is also an end to side anastomosis.

By grafting the arterial graft 12 to artery 26 in such a manner, a bypass of the artery through the arterial graft is created. Blood is therefore permitted to flow simultaneously through artery 26 and arterial graft 12. The blood flowing through arterial graft 12 will also flow through arterial port casing 8 through the open midsection of arterial graft 12. A self-sealing insert 28, such as a rubberized silicone insert or the like, inserted within the opening 10 of arterial port casing 8 prevents this blood from flowing out through the opening 10 of arterial port casing 8.

When arterial port 4 is not being used for actual dialysis procedures, blood will continuously flow through arterial graft 12 in a parallel system to that of the blood flowing through artery 26, and will then continue to flow throughout the remainder of the body. Because none of the blood within arterial graft 12 is permitted to remain stagnant, no clotting should occur.

If preferred, the two grafts may also be conducted in end-to-end anastomosis. In either event, blood will be permitted to continuously flow through the arterial graft 12, so as to help eliminate clotting therein.

As previously stated, the implantable dialysis port 2 of the first embodiment also includes a venous port 6 connected to the arterial port 4. Venous graft 18, extending from venous port 6, comprises a first end 30 and a second end 32. The first end 30 is attached to the venous port casing 14 and is in direct fluid communication with opening 16. The second end 32 is typically grafted to a vein 34 within the human body in an end to side anastomosis. Connection of the venous graft 18 may also be conducted by a large bore cannulation of a central vein, if so desired. In addition, the venous graft 18 may take the form of a venous catheter and may be inserted directly into a vein 34 so its end 32 may extend into the central venous system. Although continued reference may be made to venous grafts 18 throughout this text, it is to be understood that such references may also be interpreted as allowing for the use of venous catheters as well. Each of these types of connections are well known in the art.

As with arterial port casing 8, venous port casing 14 also contains a self-sealing insert 36 within its opening 16. This self-sealing insert 36 prevents blood from flowing through opening 16 of venous port casing 14. Once venous graft 18 is anastmosed to vein 34, blood may freely flow from vein 34 through venous graft 18. Because venous graft 18 is constructed in a "dead end" relationship with venous port 6, blood may remain stagnant within the venous port 6 and venous graft 18 once the dialysis procedure is completed and the venous port 6 is sealed. It will be appreciated that the likelihood of blood being recycled back to vein 34 from first end 30 of venous graft 18 is inversely proportional to the length of the venous graft.

It is well known in the art that stagnant blood may clot. To avoid the risk of clotting, the entire track from venous port 6 through venous graft 18 is preferably flushed with a saline solution. A pre-metered volume, approximately equal to the volume of the venous graft 18, of heparin or other anti-clotting agent may then be injected into the venous graft. Thus, blood is completely displaced from the venous port 6, opening 16 and venous graft 18 and is replaced with the anti-clotting agent. Upon start-up of the next dialysis procedure, the anti-clotting agent is permitted to flow from the body through the venous port 6 until fresh blood appears. The venous catheter 104 may then be connected to the dialysis machine 106 for initiation of the dialysis procedure. Similar procedures are well known in the medical industry. Because of the limited life-span of the self-sealing insert 36, it is preferred that a single needle be utilized to withdraw the blood, flush the line, and fill the line with heparin.

As shown in FIG. 2, the flow of blood through the arterial port 4 will generally be in the direction of arrows A, away from the heart, while the flow of blood through venous port 6 will generally be in the direction of arrows B, toward the heart.

Figure 3:
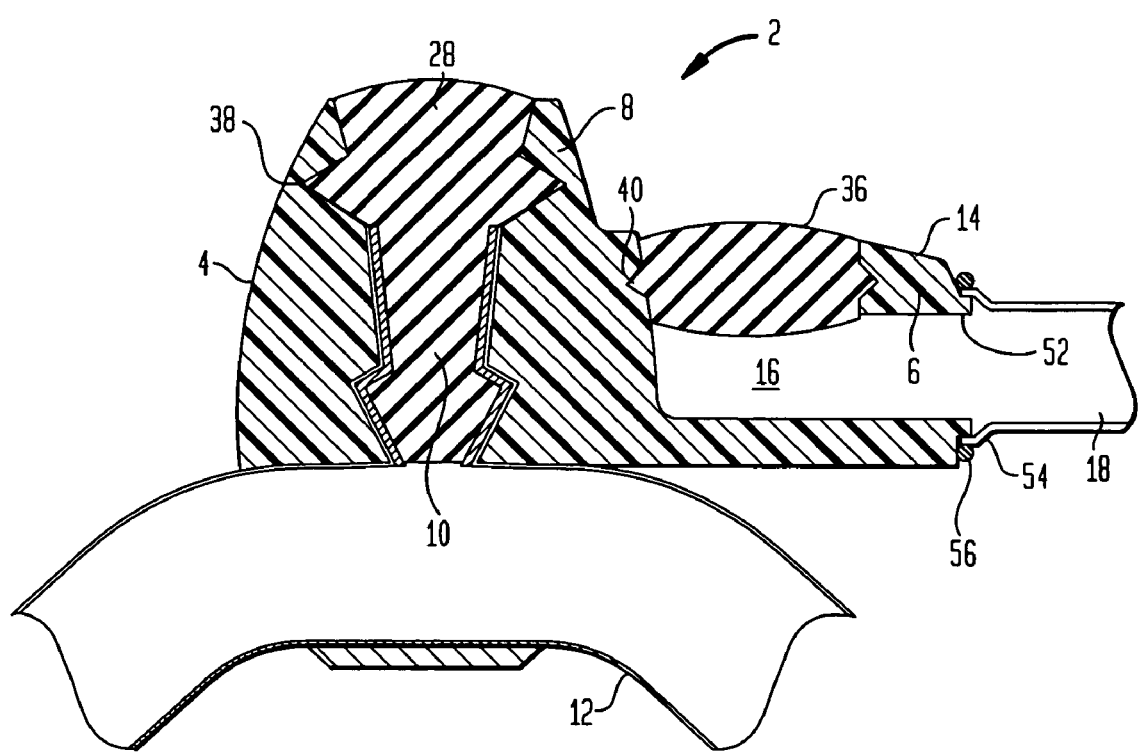
FIG. 3 is a cross-sectional view of the implantable access port of FIG. 2 taken along section lines A—A.

FIG. 3 illustrates a cross section of the implantable dialysis access port 2 of FIG. 1, taken along section line A—A of FIG. 1. As can be seen, the arterial port 4 and venous port 6 of the implantable dialysis access port 2 may be constructed monolithically, so to form an integral unit. As will be described hereinafter, the arterial port 4 and the venous port 6 may also be constructed separately. If so constructed, they may remain separate when placed in the body, or may be adaptable such that they can be connected to form one unit.

The arterial and venous port casings 8, 14 are generally constructed of a dense material such as plastic, stainless steel, or titanium, so as to be impenetrable by a needle. The material must also be compatible with implantation within the human body. The shape of the port casings 8, 14 must also be compatible with implantation into the human body. Accordingly, there preferably are no sharp edges.

The arterial and venous grafts 12, 18 must also be constructed of biocompatible material. As well known in the industry, such grafts may be formed from expanded polytetrafluroethylene (PTFE), teflon or polyester.

As may also be seen in FIG. 3, the opening 10 of arterial port casing 8 preferably comprises a plurality of indented regions 38, or other surface irregularities, into which the self-sealing insert 28 may fit. The indented regions 38 assist to prevent the self-sealing insert 28 from being pulled from the arterial port casing 8 upon removal of a needle or being pushed into arterial graft 12 upon insertion of a needle, or otherwise becoming dislodged.

Venous port casing 14 of venous port 6 is constructed in much the same manner as arterial port casing 8 of arterial port 4. In this regard, port casing 6 may include a plurality of indented regions 40 for the purpose of securing self-sealing insert 36 there within.

Figure 4:
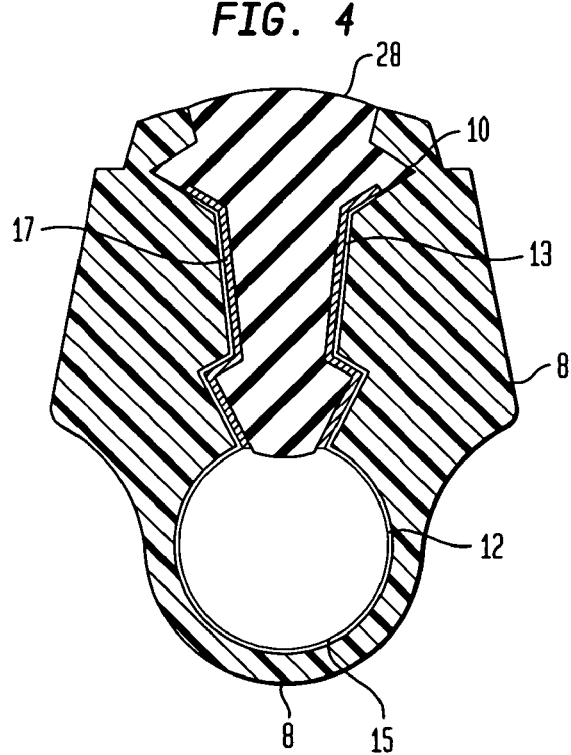
FIG. 4 is a cross-sectional view of the implantable access port of FIG. 2 taken along section lines B—B.

FIG. 4 depicts a more detailed cross sectional view of arterial port 4 in accordance with the first embodiment of the present invention taken along section line B—B of FIG. 1. In this view, it can be clearly seen that arterial graft 12 contains a branch portion 13 extending into opening 10 of arterial port casing 8. The branch portion 13 of arterial graft 12 is either formed integrally with arterial graft 12 during the manufacturing process, or is grafted on in an end to side anastomosis prior to being installed into opening 10. Preferably, the branch portion 13 extends beyond at least one of the indented regions 38. When extending so, self-sealing membrane 28 will preferably provide sufficient pressure to secure branch portion 13 in place. Biocompatible adhesives may also be applied between the branch portion 13 of arterial graft 12 and the arterial port casing 8 to assist with securing of the branch portion 8 to the arterial port casing.

Casing 17, preferably formed of metal or other puncture resistant material, may also be included between the self-sealing insert 28 and the branch portion 13 of arterial graft 12. The casing 17 may be provided to help prevent penetration, tearing, or other damage of the branch portion 13 of arterial graft 12 by the needle used during hemodialysis.

Referring back to FIG. 3, the venous graft 18 may be connected to the venous port 6 in a different manner. In a preferred embodiment, venous port casing 14 includes a spout 52 having a diameter slightly smaller than that of venous graft 18. Venous graft 18 is fitted over the entire spout 52 to form a shoulder area 54. The shoulder area 54 is then held in place by a compression ring 56, or other type of pressure fitting. The compression ring 56 may be a simple rubberized O-ring or may be a more elaborate fixture, such as a stainless steel clamp. Either way, the pressure fitting should be sufficient to prevent the ingress or egress of fluids past the connection. The fitting should also be of sufficient strength to completely secure the venous graft 18 to the spout 52.

Referring back to FIG. 4, it will be appreciated that portions of arterial port casing 8 fall below arterial graft 12 in this embodiment of the invention. One purpose of having arterial port casing 8 completely surround arterial graft 12 is to prevent a needle from piercing through the lower portion 15 of arterial graft 12 when the implantable dialysis port 2 is in use. The lower portion also prevents the arterial graft 12 from collapsing when a needle is inserted into the self-sealing membrane 28. Preferably, any such needle will be calibrated so that it is not long enough to puncture the arterial graft 12, but is long enough to enter the graft and come in contact with the blood flowing therein.

As shown in FIG. 2, arterial port casing 8 and venous port casing 14 are each shown with securing members 44. Each of these securing members 44 extend from the respective arterial or venous port casing 8, 14 and forms an aperture 46 there within. One purpose of the securing member 44 is to permit a surgeon to secure the implantable dialysis access port 2 within the body of the patient. Such securing may be conducted by suturing or stapling the securing member to tissue within the patient's body. Preferably, at least two such securing members are provided per arterial or venous port casings 8, 14. This allows for a total of four tie-down points to secure the implantable dialysis port 2 in position, which is typically sufficient to prevent detachment.

Figure 5:
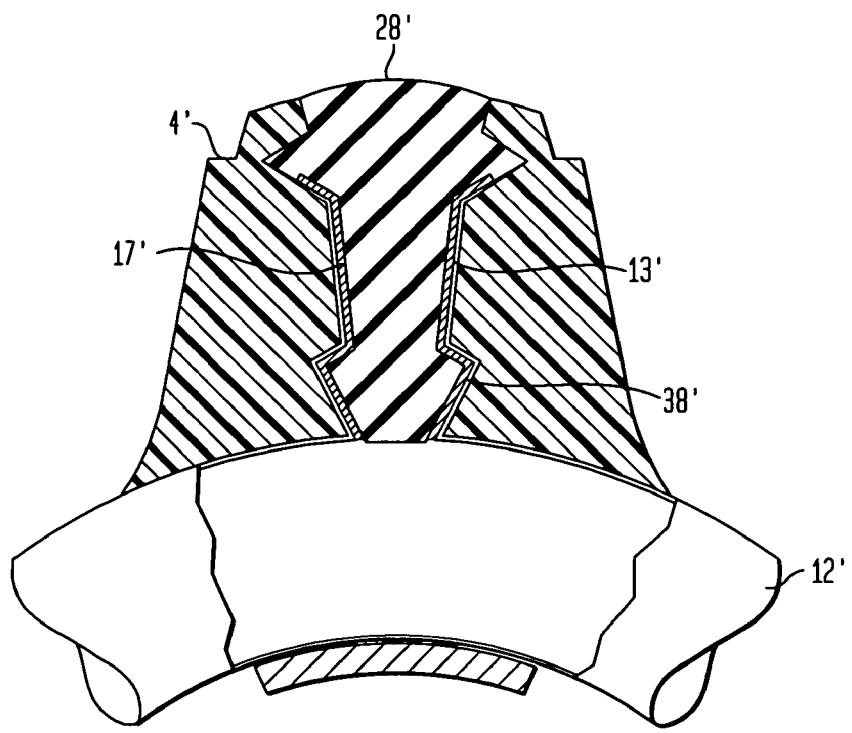
FIG. 5 is cross-sectional view of an implantable access port in accordance with another embodiment of the present invention.

FIG. 5 depicts a cross-sectional view of an arterial port casing 4' formed independent of the venous port casing (not shown). This port casing 4' is otherwise constructed similarly to the port casings previously discussed, complete with self-sealing insert 28', indented regions 38', branch portion 13', casing 17', and arterial graft 12'. As will be shown, arterial port casings 4' of this type may be accompanied by separate venous port casings 6'.

Figure 6:
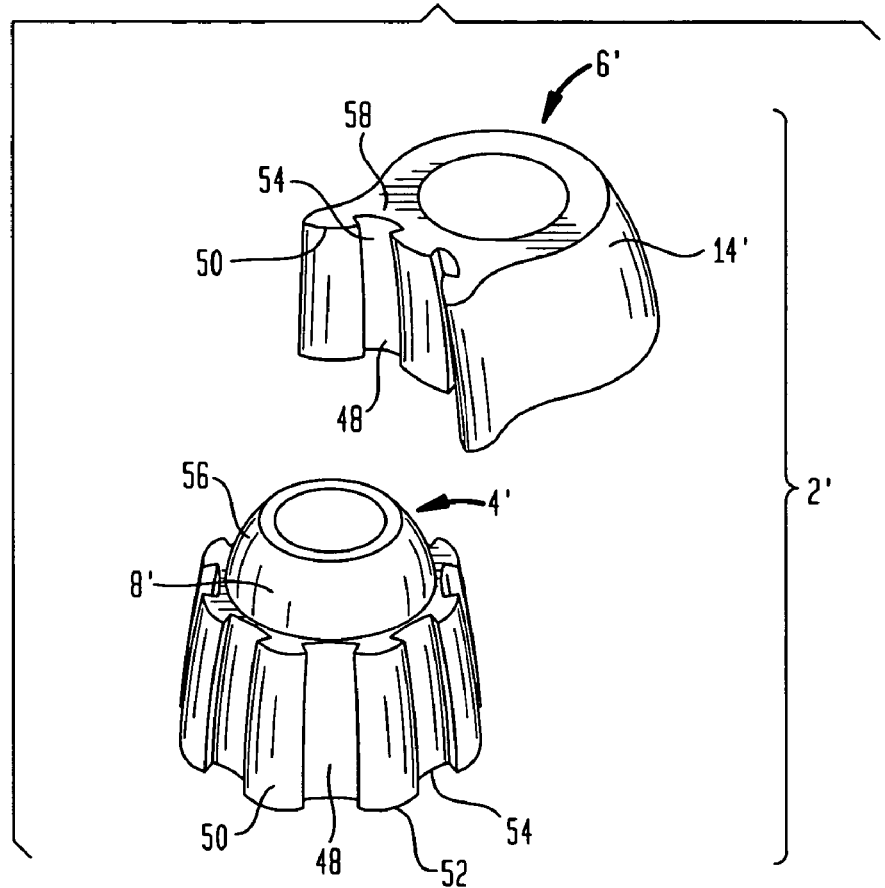
FIG. 6 is a perspective view of an implantable access port in accordance with yet another embodiment of the present invention shown in an unassembled position.

FIG. 6 depicts an implantable dialysis access port 2' in accordance with a further embodiment of the present invention. Like the embodiment shown in FIG. 5, in this embodiment the arterial port 4' and venous port 6' are constructed as two separate elements. Each port 4', 6' includes a plurality of elongate protruding ribs 50 and a plurality of elongate receiving ribs 48. Each of the protruding ribs 50 may flare outward from the respective port 4', 6' to form bulbous extending portions 52. In the meantime, each of the receiving ribs 48 may extend inward of the port 4', 6' to form bulbous receiving portions 54 sized and shaped in registration with the bulbous extending portions 52.

Preferably, one port 4', 6' includes receiving ribs 48 and protruding ribs 50 alternating around its entire exterior surface while the other port 4', 6' includes such alternating ribs only along a single side, which preferably has a shape corresponding to that of the other element. For example, in the embodiment shown in FIG. 6, the arterial port casing 8' of arterial port 4' includes ribs 48, 50 around its entire exterior surface while venous port casing 14' of venous port 6' includes such alternating ribs 48, 50 only along a single side, which has an arcuate surface corresponding to the rounded surface of arterial port 4.

The receiving ribs 48 of venous port 6' are in registration with the protruding ribs 50 of arterial port 4' and the protruding ribs 50 of venous port 6' are in registration with the receiving ribs 48 of arterial port 4' to facilitate engagement of the two structures. If arterial port 4' is provided with receiving ribs 48 and protruding ribs 50 around its entire exterior surface, it will be appreciated that venous port 6' may then be engaged with arterial port 4' in a number of axes of rotation. Such an arrangement is preferential as it permits a surgeon to strategically place the venous port 6' in relation to the arterial port 4' in accordance with the particularities of the individual into which the implantable dialysis access port 2' is to be implanted.

Figure 7:
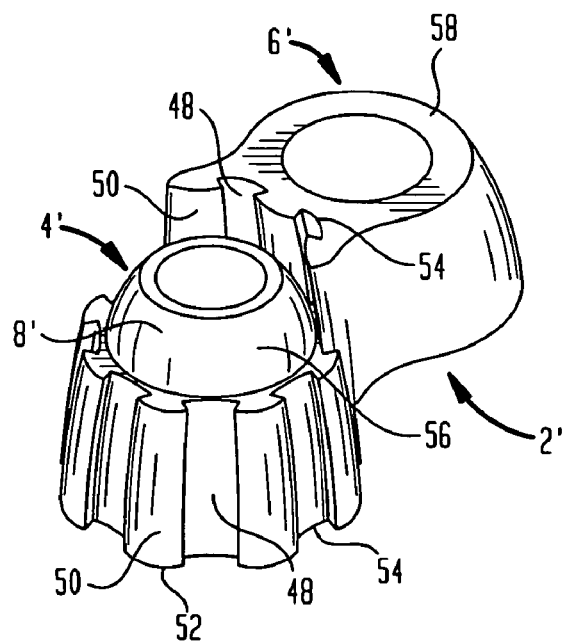
FIG. 7 is a perspective view of the implantable access port of FIG. 6 shown in a partially assembled position.

As shown in FIG. 7, in order to connect to arterial port 4' to the venous port 6', the two ports should be aligned such that the protruding ribs 50 of the venous port 6' align with the receiving ribs 48 of arterial port 4'. Once aligned, the venous port 6' may be slid relative to the arterial port 4' to engage the two to each other. It will be appreciated that the bulbous protruding portion 52 will completely fill the bulbous receiving portion 54 of the respective receiving rib 48.

It is also a feature of this invention that the arterial port 4' and the venous port 6' may be implanted in different areas of the patient. For example, one port 4', 6' may be implanted in the left shoulder area while the other port 4', 6' is implanted in the right shoulder area. This will not alter the efficiency of dialysis. Rather, the ports 4', 6' may be implanted in this manner to achieve greater patient comfort. There is no requirement that the ports 4', 6' be in connected to each other, or even in proximity to each other.

It will be appreciated that the ports 4', 6' shown in FIGS. 6 and 7 include an arterial graft (not shown) and a venous graft (not shown), respectively. Neither of these grafts has been shown in FIGS. 6 and 7 for clarity. Notwithstanding, each may be provided in accordance with the techniques previously discussed with respect to the various other embodiments of the present invention.

Figure 8:
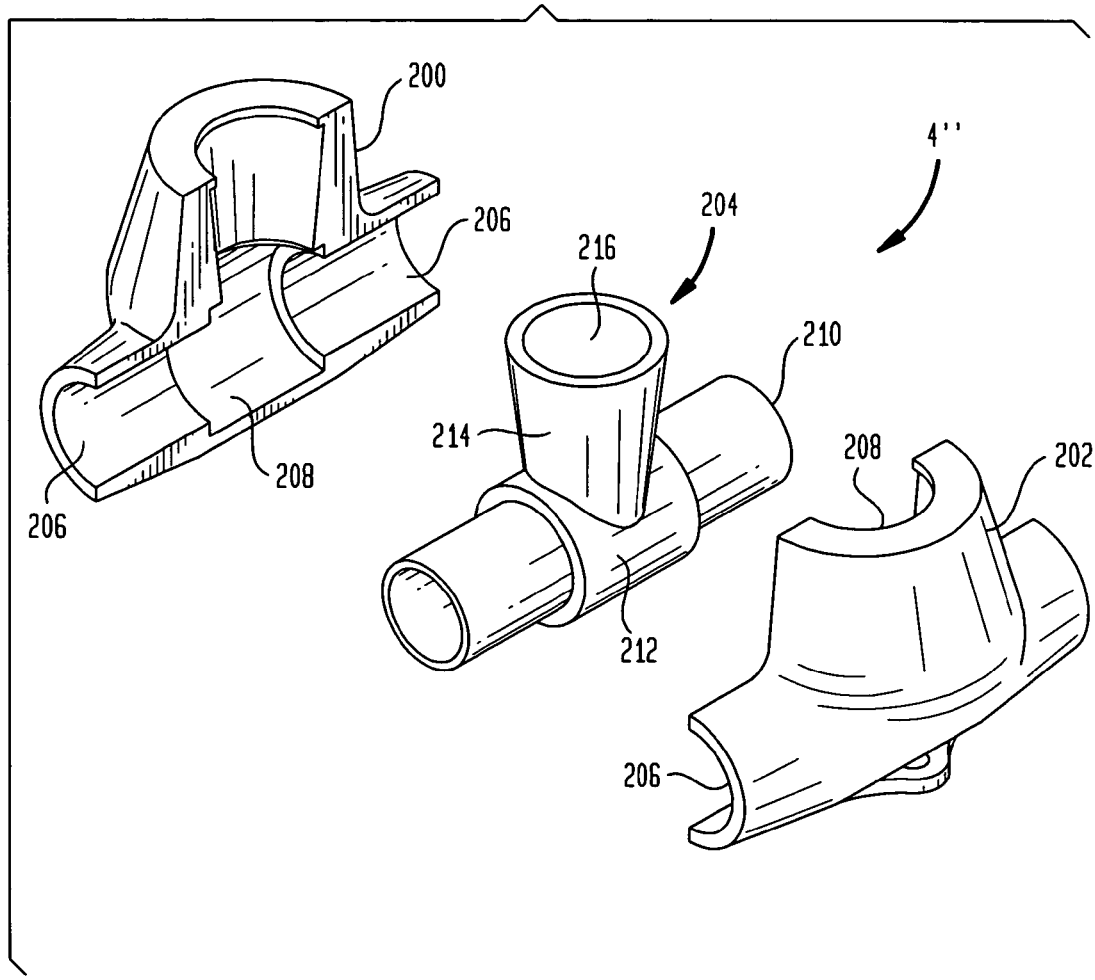
FIG. 8 is an exploded view of another embodiment of the implantable access port of the present invention; and, FIGS. 9a–d are perspective views depicting one method of installing an implantable access port constructed in accordance with another embodiment of the present invention.

FIG. 8 depicts a perspective view of yet another embodiment of the present invention. In this embodiment, the arterial port 4" is provided in three parts, a first arterial port half 200, a second arterial port half 202, and an arterial port core 204.

The first arterial port half 200 and the second arterial port half 202 may be combined to form a complete outer shell of the arterial port 41". Each arterial port half 200, 202 comprises an arcuate portion 206 forming a shaped opening, such as a complete cylinder when combined. Each arterial port half 200, 202 also comprises a second arcuate portion 208 forming a chamber generally running perpendicular to the complete cylinder. The chamber and the complete cylinder are in fluid communication with each other, and overlap in portions of each.

The arterial port core 204 comprises a graft 210 extending through a cylindrical lower casing 212. The graft 210 may be secured to the cylindrical lower casing 212 with a biocompatible adhesive or mechanically. Mounted upon the cylindrical lower casing 212, or formed integrally therewith, may be a cone-shaped upper section 214. The cone-shaped upper section may be filled with a self-sealing insert 216, supported therein by surface irregularities or biocompatible adhesives, as in other embodiments of the present invention.

In other embodiments of the invention, one half of arterial port core 204 may include a venous port coupled to its exterior surface, or may otherwise be adapted to accept a venous port being coupled to its exterior surface.

Figure 9A:
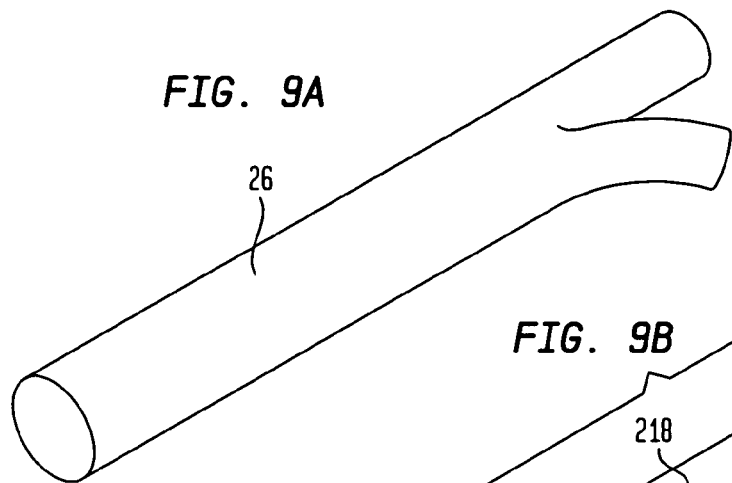
Figure 9B:
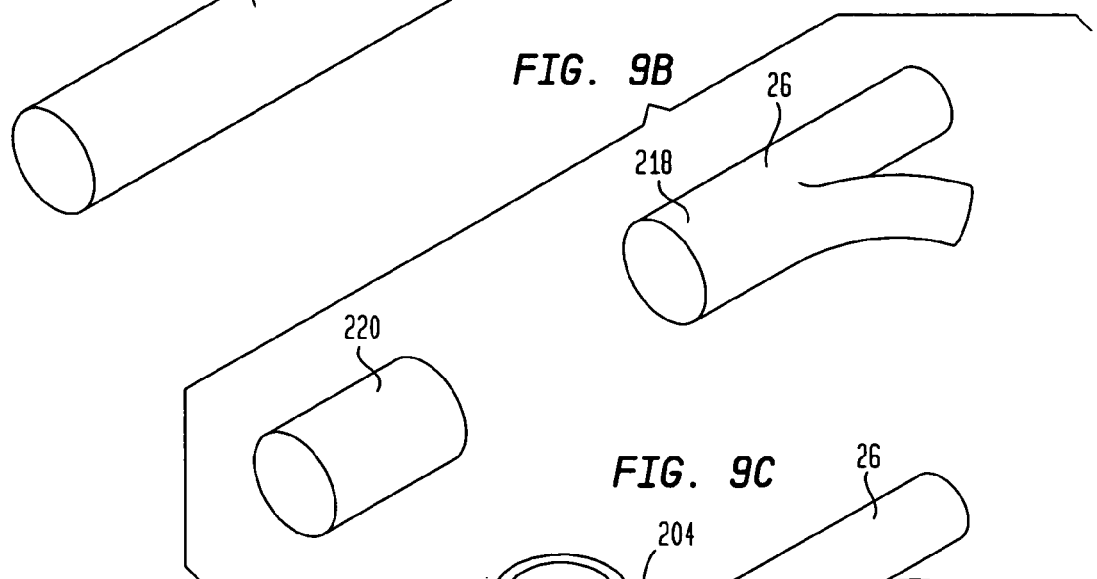
Figure 9C:
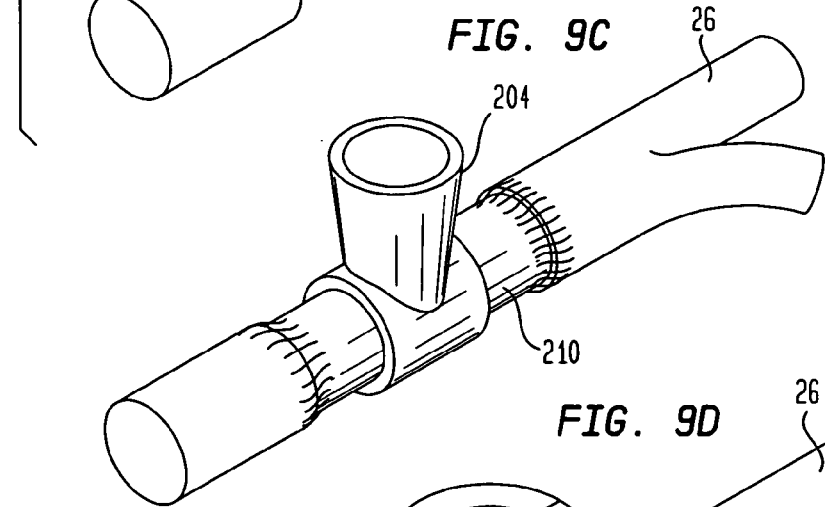
Figure 9D:
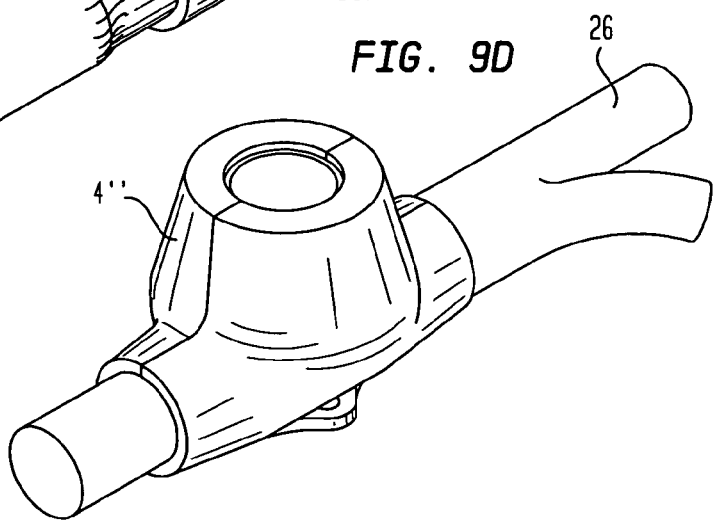

As shown in FIGS. 9a through 9d, the arterial port 411 may be implanted into the body of a mammal. To achieve such implantation, an artery, such as artery 26 shown in FIG. 9a, may be severed in two to form a first artery end 218 and a second artery end 220, as shown in FIG. 9b. Preferably, the artery 26 is at least a medium sized artery of approximately 6 to 8 mm in diameter. As shown in FIG. 9c, the graft 210 of the arterial port core 204 may be anastamosed to the first artery end 218 and the second artery end 220 such that it is interposed therebetween to permit blood to flow from the first artery end 218 to the graft 210 and then through the second artery end 220, or vice-versa. Because the entire port is not installed in this step, the gap in the artery may be as little as approximately 2 cm, rather than the approximately 6 cm that would be required if the entire port were implanted at this time. The first arterial port half 200 and the second arterial port half 202 may then be placed around the combination such that the arcuate portions 206 surround the graft 210 and the second arcuate portions 208 surround the cylindrical lower casing 212 and the cone-shaped upper section 214. As shown in FIG. 9d, the fist arterial port half 200 may then be snapped together with the second arterial port half 202 to form the complete arterial port 4".

It will be appreciated that methods of connecting the two port halves 200, 202 to each other are well known in the industry and include snap closures, as well as other mechanical fixation methods such as nuts and bolts, screws, biocompatible adhesives, and the like. If mechanical devices are utilized, they may be coated after installation with a biologic glue or silicone to prevent tissue growth. It will be appreciated that once complete, the arterial port 4" may be used in the same manner and for the same procedures as described with regard to other aspects of the present invention, including hemodialysis through puncturing of the semipermeable membrane 216.

The arterial port 4" is preferably of a sufficient length to completely cover and protect the anastomosis between the graft and the artery at each location.

As previously discussed, implantation techniques suitable for implanting the implantable dialysis access ports 2 in accordance with certain embodiments of the present invention are well known in the medical arts. The implantable dialysis access port 2 is typically implanted subcutaneously in the shoulder area below the clavicle, although it may also be implanted elsewhere in the body. It is placed such that the self-sealing insert 28 of arterial port 4 and self-sealing insert 36 of venous port 6 face outward from the chest, just below the surface of the skin. Preferably, these ports 4, 6 are located at slightly different elevations, as shown in FIG. 1, or are constructed of different geometries, such as shown in FIGS. 6 and 7 where the arterial port 4' includes a domed head 56 and the venous port includes a flat upper surface 58. The purpose of providing a distinction between the two ports 4, 6 is so that a dialysis technician, or other medical personnel, may identify each port 4, 6 during the dialysis procedure by applying slight pressure to the skin with her fingers to discern the elevation and/or shape. As previously discussed, the arterial port 4 should be hooked up to the input of the dialysis machine and the venous port 6 hooked up to the output to take advantage of the pumping power of the patient's heart.

Referring back to the embodiment shown in FIG. 2, after implantation of the ports 4, 6, the first end 20 and second end 22 of arterial graft 12 may be grafted to artery 26. Techniques for such end to side grafts are well known in the industry and may be employed. It will also be appreciated that end-to-end anastomosis may also be utilized. Once the grafts are in place, blood will be permitted to flow through arterial graft 12 which is in direct fluid communication with opening 10. However, blood is prevented from escaping from arterial port casing 8 by the placement of self-sealing insert 28. Similarly, venous graft 18 may be grafted upon vein 34 to permit blood to flow from vein 34 through venous graft 18 which is in direct fluid communication with opening 16. Blood is prevented from flowing past arterial port casing 8 by virtue of the placement of self-sealing insert 36. Once the arterial graft 12 and venous graft 18 are in place, the implantable dialysis access port may be sutured or stapled into its final placement utilizing securing members 44, as previously discussed. The patient's skin may then be sutured and the patient permitted to heal.

As best shown in FIG. 4, self-sealing insert 28, conforms to the internal shape of the port casing within which it is placed, in this case arterial port casing 8. The self-sealing insert, 28 is typically formed from rubberized silicone. Other materials may also be used, so long as the material is sufficiently elastic so as to seal against the back pressure of the blood when the implantable dialysis port 2 is not being used for dialysis, so long as it is compatible with placement inside the human body, and so long as it will self-seal upon removal of a needle, among other required qualities. Preferably, the self-sealing insert 28 will be able to remain self-sealing through a lengthy lifespan and numerous needle punctures.

Dialysis on a patient who has the implantable dialysis access port 2 previously installed is intended to be relatively simple and nearly pain free. On the patient's scheduled dialysis day, either the patient or a technician locates the implantable dialysis access port 2 just below the surface of the patient's skin. Because the arterial port 4 and venous port 6 are on different elevations, are shaped differently or are at different locations in the body, they can be distinguished from one another easily. Once they are located and distinguished, the patient or technician must pierce the patient's skin and self-sealing membrane 28 of the arterial port 4 with a needle and arterial catheter assembly 102 to permit uncleansed blood from the body to flow into the dialysis machine 106. Similarly, the patient or technician must pierce the patient's skin and the self-sealing membrane 36 of the venous port 6 with a needle and venous catheter assembly 104 to enable cleansed blood from the dialysis machine 106 to be returned to the body. Such piercing may initially be conducted with the aid of a local anesthetic to alleviate any pain the patient may endure. However, after several iterations of the process, a desensitized callous should form which may then be pierced such that no local anesthesia will be required upon subsequent punctures.

It will be appreciated that the needle used for this technical procedure is preferably a side port non-coring type needle. This type of needle allows blood to either enter or exit the needle from the side of the needle, but will not cause extensive damage to the self-sealing insert 28, such as would be caused by a coring type needle.

Following the dialysis procedure, the arterial catheter 102 transferring blood from the body to the dialysis machine 106 may be removed. The venous catheter 204 transferring blood from the dialysis machine 106 to the body may be separated from the needle puncturing the self-sealing insert 36 of the venous port 6. The venous port 6 may then be flushed with a saline solution. Finally, a metered amount of anti-clotting agent, such as heparin, may be injected. The heparin injected should be sufficient to displace all of the blood from within the venous port 6 and venous graft 18. The heparin should be sufficient to prevent clotting of blood within these areas between dialysis sessions.

Typically, each of the elements of the implantable dialysis port 2 will last for the lifetime of the patient. Thus, the implantable dialysis port 2 may remain in a single implanted location. Nevertheless, if one element fails, it will typically be one of the grafts 12, 18. Even if a graft 12, 18 fails, the implantable dialysis port 2 may remain in the same location after the graft is surgically repaired, using conventional methods known in the medical arts.

As stated, the invention provides an arterial port 4 in direct fluid communication with an artery 26 and a venous port 6 in direct fluid communication with a vein 34. This permits the invention to be very efficient, as blood is drawn off and returned to different systems within the body. In addition, it permits use of dialysis machines with less powerful pumps, as much of the energy required to pump the blood is provided by the heart. In fact, for some individuals, a pump will not be required as the natural pressure gradient between the arterial and venous systems may be sufficient to drive the blood through the complete system. Because an external pump may not be required, the heart may not be subjected to an increased pressure output.

Additionally, because blood from the venous and arterial systems is used there is no risk of ischemia due to esteal syndrome, as with methods of the prior art. There is also no risk of destruction of the local venous system.

In addition to use of the self-sealing inserts such as self-sealing insert 28, it will be appreciated that various mechanical valves may also be utilized. Such valves should serve the purpose of preventing unwanted blood flow from within the port 4, 6, while permitting selective entry of a catheter device for blood input or output. Such valves should also be provided with self-sealing abilities.

It will also be appreciated that a single implantable dialysis port, configured with a "pass through" type graft such as arterial access port 4, may have uses other than for dialysis. Such uses include situations where patients require frequent vascular injections or infusions of therapeutic fluids. Other uses include situations where a patient may require constant monitoring of blood gases or frequent drawing of blood, such as patients relying on in-home cardiac support systems. In such cases, the single port may be implanted and utilized to assist with the procedures.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implantable access port comprising:
   a port casing having a first channel extending therethrough and a second channel extending from said first channel to an exterior surface of said port casing;
      a graft having a first end and a second end, said graft disposed within said first channel of said port casing such that said first end and said second end are exterior to said port casing, said graft having a third end disposed within said second channel;
      a self-sealing insert adapted to prevent fluid from passing disposed within said second channel such that said third end of said graft is between said self-sealing insert and said port casing;
      wherein said first end and said second end of said graft are adapted to be anastomosed to a blood-carrying vessel such that blood will continuously flow through said port casing.

2. The implantable access port of claim 1, wherein said self-sealing insert is adapted to be penetrated by a needle and catheter system to transfer fluids into or out of the artery through said port casing.

3. The implantable access port of claim 2, wherein said transfer of fluids is the removal of blood from within the artery.

4. An implantable access port comprising:
   first and second port halves capable of being connected to each other and a port core adapted to be disposed between said first and second port halves when said first and second port halves are connected to each other;
   said first and second port halves each comprising a first recess channel and a second recess channel, wherein said first recess channel of said first port half and said first recess channel of said second port half generally form a shaped opening when said first and second port halves are connected to each other and said second recess channel of said first port half and said second recess channel of said second port half generally form a chamber in which said port core is disposed when said first and second port halves are connected to each other;
   said port core comprising an upper section having an aperture filled with a self-sealing insert and a lower section having an aperture with a graft disposed therethrough, said graft extending from within said shaped opening when said first and second port halves are connected to each other.

5. The implantable dialysis port of claim 4, wherein said graft further comprises a first end adapted to be anastomosed to a first vessel and a second end adapted to be anastomosed to a second vessel.

6. The implantable dialysis port of claim 5, wherein said first and second vessel are an artery of a mammal.

7. An implantable access port comprising:
   a port core having an upper section and a lower section, said upper section having an upper section channel extending therethrough, said lower section having a lower section channel extending therethrough, said upper section channel and said lower section channel in fluid communication;
   a self-sealing insert disposed within said upper section channel;
   a graft extending through said lower section;
   a first port half and a second port half, said port halves adapted to be brought together to at least partially surround said port core.

8. The implantable access port of claim 7, wherein portion of said graft also extends into said upper section channel.

9. The implantable access port of claim 8, wherein said self-sealing insert is deposed at least partially within said portion of said graft extending into said upper section channel.

10. The implantable access port of claim 8, wherein at least one of said port core and said outer casing is adapted to prevent a needle from piercing said graft.

11. The implantable access port of claim 10, further comprising an insert within said upper section channel between said portion of said graft extending into said upper section channel and said self-sealing insert, said insert being impenetrable by a needle so as to protect said graft from damage.

12. The implantable access port of claim 7, wherein said first port half includes a securing member to permit securing of the implantable access port within the body of a patient.

13. The implantable access port of claim 7, wherein the upper section channel includes at least one indented region.

14. The implantable access port of claim 13, wherein said self-sealing insert is adapted to fit within said at least one indented region.

15. The implantable access port of claim 7, wherein the upper section channel includes surface irregularities.

16. The implantable access port of claim 7, wherein said graft is constructed of one of expanded polytetrafluroethylene, teflon, and polyester.

17. The implantable access port of claim 7, wherein said port halves surround portions of said graft beyond the limits of said port core.

* * * * *